United States Patent [19]

Elliott et al.

[11] Patent Number: 4,939,292

[45] Date of Patent: Jul. 3, 1990

[54] SYNTHESIS OF ESTERS FROM ALCOHOLS CONTAINING CARBON MONOXIDE AS AN IMPURITY

[75] Inventors: David J. Elliott; Filippo Pennella, both of Bartlesville, Okla.

[73] Assignee: Phillips Petroleum Company, Bartlesville, Okla.

[21] Appl. No.: 782,779

[22] Filed: Oct. 2, 1985

Related U.S. Application Data

[63] Continuation-in-part of Ser. No. 761,444, Aug. 1, 1985, abandoned.

[51] Int. Cl.⁵ .................... C07C 67/40; C07C 69/06; C07C 69/14; C07C 69/24
[52] U.S. Cl. .................................. 560/239; 560/232; 568/485; 568/487; 568/902
[58] Field of Search .............................. 560/232, 239

[56] References Cited

U.S. PATENT DOCUMENTS

| | | | |
|---|---|---|---|
| 1,975,853 | 10/1934 | Lazier | 260/106 |
| 2,504,497 | 4/1950 | Charles et al. | 252/463 |
| 3,149,166 | 9/1964 | Pochler et al. | 260/586 |
| 3,188,330 | 6/1965 | Hecker et al. | 260/410.6 |
| 3,372,986 | 3/1968 | Sennewald et al. | 23/151 |
| 3,397,154 | 8/1968 | Talsma | 252/463 |
| 3,739,020 | 6/1973 | McClain et al. | 260/531 R |
| 3,816,513 | 6/1974 | Wakamatsu et al. | 560/232 |
| 3,856,856 | 12/1974 | Nozaki | 562/519 |
| 3,935,018 | 1/1976 | Ray et al. | 106/47 R |
| 3,956,185 | 5/1976 | Yagi et al. | 252/455 R |
| 4,052,424 | 10/1977 | Vanderspurt | 260/410 |
| 4,100,359 | 7/1978 | Schmerling et al. | 560/232 |
| 4,126,748 | 11/1978 | Scholz et al. | 560/239 |
| 4,149,009 | 4/1979 | Yoneoka et al. | 560/239 |
| 4,250,329 | 2/1981 | McVicker | 560/232 |
| 4,332,914 | 6/1982 | Knifton | 518/700 |
| 4,599,454 | 7/1986 | Elliot et al. | 568/387 |

FOREIGN PATENT DOCUMENTS 313575 12/1930 United Kingdom ................ 560/239

*Primary Examiner*—Vivian Garner
*Attorney, Agent, or Firm*—K. K. Brandes

[57] ABSTRACT

Esters are prepared by contacting, under suitable reaction conditions, a feed stream comprising a primary alcohol of 1–4 carbon atoms per molecule (preferably methanol, ethanol) and carbon monoxide with a catalyst composition comprising (a) copper or a copper compound (preferably CuO), (b) zinc oxide, (c) at least one metal or compound of at least one metal selected from the group consisting of cobalt, ruthenium, iridium, platinum, molybdenum, and rhenium (preferably cobalt and/or rhenium) and, optionally, (d) alumina.

36 Claims, No Drawings

SYNTHESIS OF ESTERS FROM ALCOHOLS CONTAINING CARBON MONOXIDE AS AN IMPURITY

This is a continuation-in-part application of our co-pending application having Ser. No. 761,444, filed August 1, 1985, now abandoned.

BACKGROUND OF THE INVENTION

This invention relates to a catalytic process for producing esters. In another aspect, this invention relates to the catalytic conversion of alcohols to esters.

Catalytic processes for converting alcohols to esters are well known. However, there is an ever present need to develop new, more effective processes and catalysts for converting alcohols to esters at acceptable yields, particularly when these alcohols have been prepared from synthesis gas and contain carbon monoxide as an impurity.

SUMMARY OF THE INVENTION

It is an object of this invention to catalytically convert aliphatic alcohols, preferably normal primary alcohols (straight chain primary alcohols), which contain carbon monoxide as an impurity, to esters containing at least twice the number of carbon atoms per molecule as said alcohols. It is another object of this invention to at least partially convert methanol, which contains carbon monoxide as an impurity, to methyl formate (without prior removal of CO from the alcohol feed). It is a further object of this invention to at least partially convert ethanol, which contains carbon monoxide as an impurity, to ethyl acetate (without prior removal of CO from the alcohol feed). It is still another object of this invention to provide an effective catalyst for the conversion of alcohols to esters. Other objects and advantages of the invention will be apparent from the detailed description and the appended claims.

In accordance with this invention, a feed stream comprising at least one primary aliphatic alcohol having from 1 to 4 carbon atoms per molecule and carbon monoxide is contacted with a catalyst composition comprising (a) copper or an oxide thereof, (b) zinc oxide, and (c) at least one metal or compound of a metal selected from the group consisting of cobalt, ruthenium, iridium, platinum, molybdenum and rhenium, under such conditions as to at least partially convert said primary alcohol to at least one ester containing at least twice the number of carbon atoms per molecule as contained in said primary alcohol. Preferably, the catalyst component (c) is at least one of cobalt compounds (more preferably a nitrate and/or oxide of Co) and rhenium compounds (more preferably ammonium perrhenate and/or an oxide of Re); and the primary alcohol is a normal (straight chain) primary aliphatic alcohol, more preferably methanol and/or ethanol.

In one preferred embodiment of this invention, the catalyst composition employed in the process of this invention comprises copper oxide (preferably CuO), zinc oxide, cobalt oxide and an inorganic refractory oxide support material such as alumina. In another preferred embodiment of this invention, the catalyst composition employed in the process of this invention comprises copper oxide (preferably CuO), zinc oxide, rhenium oxide and an inorganic refractory oxide support material such as alumina.

In still another preferred embodiment of this invention, the catalyst composition comprising CuO, ZnO and at least one of cobalt oxide and rhenium oxide is pretreated by heating with a reducing gas, preferably a free hydrogen containing gas, under such conditions as to partially reduce CuO to $Cu_2O$ and/or Cu metal, before the catalyst composition is used in the process of this invention.

DETAILED DESCRIPTION OF THE INVENTION

The catalyst composition employed in the process of this invention comprises (a) copper or an oxide thereof (preferably CuO), (b) zinc oxide and (c) at least one metal or compound of a metal selected from the group consisting of Co, Ru, Ir, Pt, Mo and Re, preferably cobalt oxide and/or rhenium oxide.

The cobalt-containing catalyst composition can be prepared by coprecipitation of the hydroxides and/or the carbonates of copper, zinc and cobalt, e.g. by addition of a base such as NaOH, plus optionally a soluble carbonate such as $Na_2CO_3$, to an aqueous solution of copper(II), zinc and cobalt(II) salts (such as the nitrates, sulfates or halides), and subsequent calcination (e.g., heating in a non-reducing atmosphere, e.g., air) under such conditions as to form oxides of copper, zinc and cobalt. It is presently preferred to first prepare a CuO-ZnO composition by coprecipitation (substantially as discussed above but without a cobalt salt) and then to impregnate the calcined CuO-ZnO with a solution of a cobalt salt, more preferably cobalt nitrate, and heating the thus obtained material so as to dry it and, preferably, at least partially convert the nitrate to an oxide of cobalt.

The rhenium-containing catalyst composition can be prepared by coprecipitation of the hydroxides and/or the carbonates of copper, zinc and rhenium, e.g. by addition of a base such as NaOH, plus optionally a soluble carbonate such as $Na_2CO_3$, to an aqueous solution of copper(II) and zinc salts (such as the nitrates, sulfates or halides), and at least one rhenium compound (such as $NH_4ReO_4$), and subsequent calcination (e.g., heating in a non-reducing atmosphere, e.g., air) under such conditions as to form oxides of copper, zinc and rhenium. It is presently preferred to first prepare a CuO-ZnO composition by coprecipitation (substantially as discussed above but without a rhenium compound) and then to impregnate the calcined CuO-ZnO with a solution of a rhenium compound, more preferably $NH_4ReO_4$, and heating the thus obtained material so as to dry it and, preferably, at least partially convert the nitrate to an oxide of rhenium.

In the preferred embodiments, an inert support material such as alumina is also present in said catalyst compositions, preferably prepared by either coprecipitation of hydroxides and/or carbonates of copper, zinc, at least one of cobalt and rhenium, and aluminum, and subsequent calcination under such conditions as to form oxides of copper, zinc, at least one of cobalt and rhenium, and aluminum; or by coprecipitation of hydroxides and/or carbonates of copper, zinc, and at least one of cobalt and rhenium from an aqueous solution containing alumina dispersed therein, and subsequent calcination. It is presently preferred to first prepare a CuO-ZnO-$Al_2O_3$ composition by coprecipitation (substantially as discussed above but without a cobalt or rhenium compound) and then to impregnate the calcined CuO-ZnO-$Al_2O_3$ composition with a solution containing a cobalt salt, more preferably cobalt nitrate, and/or a rhenium compound, more preferably ammonium perrhenate ($NH_4ReO_4$) and heating the thus obtained material so as to dry it and, preferably, at least partially convert cobalt nitrate to an oxide of cobalt and/or ammonium perrhenate to an oxide of rhenium.

In a preferred embodiment, the CuO/ZnO/cobalt CuO/ZnO/cobalt/$Al_2O_3$, CuO/Zn/rhenium and CuO/ZnO/rhenium/$Al_2O_3$ containing catalyst compositions are pretreated before use by heating with a reducing gas, preferably a free hydrogen containing gas, so as to partially reduce CuO (to $Cu_2O$ and/or Cu metal). More preferably, said heating is carried out with a free hydrogen containing gas, most preferably a $H_2/N_2$ mixture containing 2-5 volume-% $H_2$, at about 350°-450° F. for about 1-6 hours.

Preferably the atomic ratio of Cu to Zn in the catalyst compositions is in the range of from about 1:20 to about 20:1, more preferably from about 1:3 to about 3:1. When Co is present in the catalyst composition, preferably the atomic ratio of the Co to Cu is in the range of from about 1:10,000 to about 10:1, more preferably from about 1:1,000 to about 1:10, most preferably from about 1:200 to about 1:50. When Re is present in the catalyst composition, preferably the atomic ratio of Re to Cu is in the range of from about 1:50,000 to about 10:1, more preferably from about 1:5,000 to about 1:20, most preferably from about 1:200 to about 1:50. Even though it is presently preferred, to have either Cu or Re present in the catalyst invention, it is within the scope of this invention to have both Cu and Re present at the above Co:Cu and Re:Cu atomic ratios.

If alumina or another inert refractory material (e.g., silica, an alumino-silicate, titania, magnesia and the like) is also present in said catalyst composition, the ratio of the weight of said inert material such as alumina to the combined weight of compounds of Cu, Zn and at least one of Co and Re can range from about 1:100 to about 10:1, preferably from about 1:10 to 2:1.

Generally the surface area (determined by the BET/$N_2$ method, ASTM D3037) of the finished catalyst composition ranges from about 20 $m^2/g$ to about 300 $m^2/g$, preferably from about 50 $m^2/g$ to about 200 $m^2/g$.

The feed mixture that is contacted with the CuO-ZnO-cobalt and/or CuO-ZnO-rhenium containing catalyst composition comprises (a) at least one primary aliphatic alcohol having from 1 to 4 carbon atoms per molecule and (b) carbon monoxide. The mole ratio of the alcohol to carbon monoxide generally ranges from about 1:1,000 to about 1,000:1, preferably from about 1:100 to about 100:1. An inert gas such as nitrogen or helium can also be present in said feed stream. Preferred primary alcohols are methanol and ethanol; and the preferred ester products are methyl formate and ethyl acetate, respectively. If more than one alcohol is employed, e.g., a mixture of methanol and ethanol, the weight ratio of the first alcohol to the second ratio can be in the range of from about 1:1,000 to about 1,000:1.

The alcohol and CO containing feed mixture can be contacted with the catalyst composition of this invention in any suitable manner. An at least partially vaporized alcohol containing stream and a carbon monoxide containing stream can be passed separately into a suitable reaction vessel and can then be contacted in at least partially mixed form with the catalyst composition under suitable reaction conditions. The alcohol containing stream can be fed as a substantially liquid stream, which will then vaporize in the reactor, or as a substantially vaporized stream. It is presently preferred that alcohol and carbon monoxide are mixed before being introduced into the reaction vessel and contacted with the catalyst composition under suitable reaction conditions so as to produce a reaction product comprising at least one ester. In one embodiment, the feed stream contains methanol and/or ethanol that has been prepared from synthesis gas and contains CO as an impurity.

The process of this invention can be carried out as a batch process or as a continuous process. In a batch process, the process ingredients are charged in any order to a vessel equipped with pressuring and heating means, and the ingredients are then kept in contact with the catalyst composition for a certain length of time under suitable reaction conditions so as to produce a product comprising at least one ester containing at least twice as many carbon atoms per molecule as the feed alcohol. In this type of operation, the catalyst can be dispersed in the feed stream as a fluidized bed; or the feed stream can be circulated through a fixed bed containing the catalyst composition. In a continuous process, which is presently preferred, a gaseous feed stream comprising the alcohol and CO is passed through a fixed bed containig the solid catalyst composition, under such conditions as will result in a product comprising at least one ester. Optionally, an inert gas can be present during the batch or continuous process.

Heating of the process ingredients is generally required to accomplish at least partial conversion of the primary alcohol to an ester. Any suitable temperature that will cause and maintain a controllable reaction can be employed. Any feasible heating means can be utilized. It is within the scope of this invention to preheat one or more of the process ingredients before they are introduced into a reactor, which is heated to maintain a suitable temperature. The reaction temperature generally is in the range of from about 200° C. to about 400° C., preferably from about 250° C. to about 300° C.

Any suitable reaction pressure can be employed. The reaction pressure generally is above atmospheric pressure. The selection of the reaction pressure will greatly depend on the reaction temperature, the feed rates of the reactants and the specific reactor design. Generally the pressure ranges from about 1 to about 5000 psig, preferably about 200 to about 2000 psig.

The reaction time, i.e., the time of intimate, simultaneous contact of all process ingredients, can vary from 0.01 to about 60 minutes, and will preferably be in the range of about 0.1 to about 10 minutes. The actual reaction time will greatly depend on the flow rates of the alcohol and CO containing feed stream, the selection of an effective, yet safe reaction temperature, the extent of mixing and agitation (if any) during the reaction, the amount of the catalyst employed, etc. In a continuous process, the gas hourly space velocity of the feed mixture comprising the primary alcohol and CO ranges generally from about 100 to about 10,000 cc feed mixture/cc catalyst/hour, preferably from about 1,000 to about 5,000 cc/cc/hr, measured at about 550° F. and 15 psia.

The formed reaction product which comprises at least one ester having at least twice as many carbon atoms as the primary alcohol from which it is formed can be separated from other components of the reaction product and unconverted alcohol by any suitable separation means such as condensation, crystallization, absorption, fractional distillation, or extraction with a suitable solvent plus subsequent evaporation of the solvent. Unreacted process ingredients can be at least partially separated in a similar manner and can be recycled to the reaction zone, where the conversion of a primary alcohol to an ester in accordance with this invention occurs.

If a reaction product containing more than one ester is formed, for instance when more than one feed alcohol is employed such as a mixture of methanol and ethanol, said mixture of esters can be separated into ester components of the mixture (such as methyl formate, methyl acetate and ethyl acetate) by any of the above-cited or other known separation means. Product compositions of the reactions of CO with the preferred alcohols (methanol, ethanol) under specific reaction conditions are presented in the examples. Esters prepared by the process of this invention can be used as solvents and/or as reactants in various organic synthesis.

The following examples are presented to further illustrate this invention without unduly limiting the scope of the invention.

EXAMPLE I

This example illustrates the conversion of a mixture of ethanol and carbon monoxide to esters, primarily ethyl acetate, in the presence of two catalysts. A 16/14 mesh CuO-ZnO-Al$_2$O$_3$ catalyst (Control *Catalyst A*) was prepared substantially in accordance with the procedure of Example I of U.S. Pat. No. 3,790,505.

Invention *Catalyst B* was prepared by impregnating 60.0 grams of Catalyst A with an aqueous solution containing 0.9 grams of Co(NO$_3$)$_2$.6H$_2$O and drying the thus impregnated material at about 140° C. overnight in a forced air oven. The atomic ratio of Co to Cu in Catalyst B was about 0.01:1.

The conversion of ethanol to esters is carried out in a vertical, tubular, stainless steel reactor having an inner diameter of about one-half inch and a catalyst bed length of about 5–6 inches, which is heated by means of an outside furnace. The reactor was filled as follows: top layer of 5 cc 16 mesh Alundum (having a surface area of less than 1 m$^2$/g; marketed by Norton Chemical Process Products, Akron, Ohio); middle layer of 2.5 cc (3.0 g) of Catalyst A or Catalyst B plus 7.5 cc 16 mesh Alundum; bottom layer of 5 cc 16 mesh Alundum. A thermocouple was axially inserted into the catalyst bed.

First the catalyst bed in the reactor was pretreated with a H$_2$/N$_2$ (3/97) gas mixture at about 390°–400° F., for a time period of about 4 hours. Then the reactor was purged with nitrogen, the reactor temperature was raised to about 540°–550° F., and two feed streams were charged to the reactor: liquid ethanol at a rate of about 2.1 cc/hour and carbon monoxide (99.5%) at a rate of 140 cc/minute, so as to provide a combined gas stream containing about 90 volume-% CO. The reaction pressure was about 1000 psig. The product stream was cooled by a cold trap having a temperature of about 40° F., so as to condense the less volatile components. The off-gas product stream was analyzed by means of a modified Applied Automation Model 12 gas chromatograph (GC), whereas the liquid product was analyzed by means of a Hewlett-Packard Model 5750 gas chromatograph with columns being packed with Porapak Q material. The various components of the liquid product separated by GC were confirmed by mass spectrometry.

The compositions of the liquid and gaseous product streams of Runs 1 and 2 are summarized in Table I. Total reaction times were 16 hours in both runs.

TABLE I

| Run | 1 (Control) | 2 (Invention) |
|---|---|---|
| Feed | Ethanol | Ethanol |
| Catalyst | A | B |
| Liquid Compounds | Weight-% | Weight-% |
| Water | 0.23 | 0.34 |
| Methanol | 11.47 | 0.96 |
| Acetaldehyde | 0.27 | 2.07 |
| Ethanol | 6.68 | 27.62 |
| Acetone | 0.22 | 1.89 |
| Methyl Acetate | 2.74 | 3.95 |
| 1-Propanol | 1.84 | 0.49 |
| Butanone | 3.63 | 5.34 |
| Ethyl Acetate | 3.04 | 34.59 |
| 2-Methyl-1-Propanol | 4.15 | — |
| 1-Butanol | 2.20 | 4.11 |
| Pentanols | — | 4.45 |
| C$_5$ Ketones | 5.79 | 1.81 |
| Methyl Butyrate | 1.78 | — |
| Not Identified | 3.41 | — |
| C$_6$-C$_7$ Alcohols | 4.58 | 9.03 |
| C$_6$-C$_9$ Ketones | 47.97 | 3.35 |
| Gaseous Compounds | Vol-% | Vol-% |
| H$_2$ | 5.08 | 5.87 |
| CO | 83.49 | 91.71 |
| CO$_2$ | 7.53 | 2.30 |
| CH$_4$ | 0.05 | 0.04 |
| C$_2$H$_6$ | 0.37 | 0.08 |

Data in Table I clearly show that only a minor amount of ethyl acetate was produced in control run 1, whereas ethyl acetate was the major liquid product component in run 2. The conversion of ethanol was about 93% in run 1 and about 79% in run 2. The selectivity to ethyl acetate (ethyl acetate yield÷ethanol conversion) was 3% in run 1 and about 48% in run 2.

EXAMPLE II

This example illustrates the conversion of methanol and carbon monoxide to esters over Catalysts A and B at conditions essentially the same as those described in Example I. The flow rate of the liquid methanol feed stream was 2.1 cc/hour, the CO flow rate was 140 cc/minute. The composition of the liquid products are summarized in Table II.

TABLE II

| Run | 3 (Control) | 4 (Invention) |
|---|---|---|
| Feed | Methanol | Methanol |
| Catalyst | A | B |
| %-Conversion[1] of Methanol | 81 | 55 |
| Liquid Compounds | Weight-% | Weight-% |
| Water | 0.9 | 0.6 |
| Methanol | 56.6 | 94.2 |
| Methyl Formate | 0.2 | 2.0 |
| Ethanol | 7.0 | 1.2 |
| Propanol | 5.2 | 0.6 |
| Butanols | 13.7 | — |
| Not Identified | 16.4 | 1.4 |

[1]to gases (hydrogen, carbon monoxide) and liquid products.

Data in Table II show that the production of methyl formate was significantly higher in run 4 employing invention Catalyst B than in run 3 employing Catalyst A.

EXAMPLE III

Tests have shown that the conversion of a mixture containing about 67 volume percent $H_2$ and 31 volume percent CO to methanol by passing the gas mixture at a rate of 7.2 liters/cc catalyst/hour over a Cu/ZnO catalyst at about 250° C./65 atm was significantly reduced when the Cu/ZnO catalyst contained about 0.3 weight-% Co (i.e., similar to Catalyst B of this invention), or about 0.5 weight-% Ru, or about 0.8 weight-% Ir or about 0.8 weight-% Pt or about 1 weight-% Mo. These test results indicate that the above-cited Group VIII metals poison those catalyst sites responsible for alcohol synthesis and would consequently promote the activity of those catalyst sites responsible for the production of other substances including esters. Based on these test results and conclusions, it is believed that Cu/ZnO catalysts which contain Ru and/or Ir and/or Pt and/or Mo would also promote the conversion of alcohols, which contain CO as an impurity, to esters as does the preferred CoO/Cu/ZnO catalyst composition of this invention.

EXAMPLE IV

Invention Catalyst C was prepared by impregnating 30.0 grams of Catalyst A with about 9 ml of an aqueous solution containing 0.39 grams of $NH_4ReO_4$ (ammonium perrhenate). The thus impregnated material was dried at about 140° C. overnight in a forced air oven. The dried catalyst C contained about 0.9 weight-% Re and possessed an atomic Re:Cu ratio of 0.01:1. The reaction pressure was about 960 psig. The compositions of liquid and gaseous product streams of Invention Run 5 are summarized in Table III and compared with those of Control Run 1 (from Table I).

Catalyst C was employed in the conversion of ethanol to esters (Run 5), substantially in accordance with the procedure described in Example I. Catalyst C was pretreated with a $H_2/N_2$ (3/97) gas mixture at 400° F. for a time period of about 4 hours. The reaction temperature, liquid ethanol feed rate and CO gas feed rate were essentially the same as in Example I. The test data in Table III clearly show that the production of ethyl acetate was significantly higher in Run 5, which employed a Re-containing CuO/ZnO catalyst, than in Run 1, which used a CuO/ZnO catalyst without Re.

TABLE III

| Run | 1 (Control) | 5 (Invention) |
|---|---|---|
| Feed | Ethanol | Ethanol |
| Catalyst | A | C |
| Liquid Compounds | Weight-% | Weight-% |
| Water | 0.23 | 3.50 |
| Methanol | 11.47 | — |
| Acetaldehyde | 0.27 | 1.60 |
| Ethanol | 6.68 | 20.90 |
| Acetone | 0.22 | 2.44 |
| Methyl Acetate | 2.74 | 9.99 |
| 1-Propanol | 1.84 | 0.96 |
| Butanone | 3.63 | 6.71 |
| Ethyl Acetate | 3.04 | 33.68 |
| 2-Methyl-1-Propanol | 4.15 | — |
| 1-Butanol | 2.20 | 2.14 |
| Pentanols | — | 3.34 |
| $C_5$ Ketones | 5.79 | 4.41 |
| Methyl Butyrate | 1.78 | — |
| Not Identified | 3.41 | — |
| $C_6$-$C_7$ Alcohols | 4.58 | 8.65 |
| $C_6$-$C_9$ Ketones | 47.97 | 1.67 |
| Gaseous Compounds | Vol-% | Vol-% |
| $H_2$ | 5.08 | 6.02 |
| CO | 83.49 | 87.58 |
| $CO_2$ | 7.53 | 3.09 |
| $CH_4$ | 0.05 | — |
| $C_2H_6$ | 0.37 | 0.15 |

Reasonable variations and modifications are possible within the scope of the disclosure and the appended claims.

We claim:

1. A process for preparing esters which comprises the steps of contacting a mixture comprising at least one primary aliphatic alcohol having from 1 to 4 carbon atoms per molecule and carbon monoxide with a catalyst composition consisting essentially of (a) copper or an oxide thereof, (b) zinc oxide, (c) at least one metal or compound of a metal selected from the group consisting of cobalt and rhenium, and (d) alumina, under such reaction conditions as to produce a reaction product comprising at least one ester having twice as many carbon atoms per molecule as the primary alcohol from which the ester is formed, and (B) separating at least a portion of said at least one ester from said reaction product.

2. A process in accordance with claim 1, wherein said primary aliphatic alcohol is a normal primary alcohol.

3. A process in accordance with claim 2, wherein said normal primary alcohol is methanol.

4. A process in accordance with claim 2, wherein said normal primary alcohol is ethanol.

5. A process in accordance with claim 1, wherein the mole ratio of said at least one primary aliphatic alcohol to carbon monoxide is in the range of from about 1:1,000 to about 1,000:1.

6. A process in accordance with claim 1, wherein the mole ratio of said at least one primary aliphatic alcohol to carbon monoxide is in the range of from about 1:100 to about 100:1.

7. A process in accordance with claim 1, wherein catalyst compound (c) is cobalt or a compound of cobalt.

8. A process in accordance with claim 7, wherein the atomic ratio of Cu to Zn in said catalyst composition is in the range of from about 1:20 to about 20:1, the atomic ratio of Co to Cu is in the range of from about 1:10,000 to about 10:1, the ratio of the weight of $Al_2O_3$ to the combined weight of compounds of Cu, Zn and Co is in the range of from about 1:100 to about 10:1, the surface area of said catalyst composition is in the range of from about 20 $m^2/g$ to about 300 $m^2/g$, and said cobalt compound is selected from the group consisting of cobalt oxide and cobalt nitrate.

9. A process in accordance with claim 7, wherein the atomic ratio of Cu to Zn in said catalyst composition is in the range of from about 1:3 to about 3:1, the atomic ratio of Co to Cu is in the range of from about 1:1,000 to about 1:10, the ratio of the weight of $Al_2O_3$ to the combined weight of compounds of Cu, Zn and Co is in the range of from about 1:10 to about 2:1, the surface area of said catalyst composition is in the range of from about 50 $m^2/g$ to about 200 $m^2/g$, and said cobalt compound is selected from the group consisting of cobalt oxide and cobalt nitrate.

10. A process in accordance with claim 1, wherein catalyst compound (c) is rhenium or a compound of rhenium.

11. A process in accordance with claim 10, wherein the atomic ratio of Cu to Zn in said catalyst composition is in the range of from about 1:20 to about 20:1, the atomic ratio of Re to Cu is in the range of from about 1:50,000 to about 10:1, the ratio of the weight of $Al_2O_3$ to the combined weight of compounds of Cu, Zn and Re is in the range of from about 1:100 to about 10:1, the surface area of said catalyst composition is in the range of from about 20 $m^2/g$ to about 300 $m^2/g$, and said rhenium compound is selected from the group consisting of rhenium oxide and ammonium perrhenate.

12. A process in accordance with claim 10, wherein the atomic ratio of Cu to Zn in said catalyst composition is in the range of from about 1:3 to about 3:1, the atomic ratio of Re to Cu is in the range of from about 1:5,000 to about 1:20, the ratio of the weight of $Al_2O_3$ to the combined weight of compounds of Cu, Zn, and Re is in the range of from about 1:10 to about 2:1, the surface area of said catalyst composition is in the range of from about 50 $m^2/g$ to about 200 $m^2/g$, and said rhenium compound is selected from the group consisting of rhenium oxide and ammonium perrhenate.

13. A process in accordance with claim 1, wherein said catalyst composition has been pretreated by heating with a reducing gas under such conditions as to partially reduce copper oxide before said contacting.

14. A process in accordance with claim 13, wherein said reducing gas is a free hydrogen containing gas, and said heating conditions comprise a temperature of about 350°–450° F. and a heating time of about 1–6 hours.

15. A process in accordance with claim 1, wherein said reaction conditions comprise a reaction temperature in the range of from about 200° to about 400° C., a reaction pressure in the range of from about 1 to 5,000 psig, and a contact time in the range of from about 0.01 to about 60 minutes.

16. A process in accordance with claim 15; wherein said reaction conditions further comprise a combined gas hourly space velocity of said mixture comprising said at least one primary aliphatic alcohol and carbon monoxide in the range of from about 100 to about 10,000 cc mixture/cc catalyst/hour, measured at about 550° F. and 15 psia.

17. A process in accordance with claim 1 comprising the additional step of (C) recycling at least a portion of said reaction product, from which at least a portion of said at least one ester has been separated in step (B), to the reaction zone.

18. A process in accordance with claim 1 wherein the formed ester is at least one of methyl formate and ethyl acetate.

19. A process for preparing esters which comprises the steps of (A) contacting a mixture comprising at least one primary aliphatic alcohol having from 1 to 4 carbon atoms per molecule and carbon monoxide with a catalyst composition consisting essentially of (a) copper or an oxide thereof, (b) zinc oxide and (c) at least one metal or compound of a metal selected from the group consisting of cobalt and rhenium, under such reaction conditions as to produce a reaction product comprising at least one ester having twice as many carbon atoms per molecule as the primary alcohol from which the ester is formed, and (B) separating at least a portion of said at least one ester from said reaction product.

20. A process in accordance with claim 19, wherein said primary aliphatic alcohol is a normal primary alcohol.

21. A process in accordance with claim 20 wherein said normal primary alcohol is methanol.

22. A process in accordance with claim 20, wherein said normal primary alcohol is ethanol.

23. A process in accordance with claim 19, wherein the mole ratio of said at least one primary aliphatic alcohol to carbon monoxide is in the range of from about 1:1,000 to about 1,000:1.

24. A process in accordance with claim 19, wherein the mole ratio of said at least one primary aliphatic alcohol to carbon monoxide is in the range of from about 1:100 to about 100:1.

25. A process in accordance with claim 19, wherein catalyst component (c) is cobalt or a compound of cobalt.

26. A process in accordance with claim 25, wherein the atomic ratio of Cu to Zn in said catalyst composition is in the range of from about 1:20 to about 20:1, the atomic ratio of Co to Cu is in the range of from about 1:10,000 to about 10:1, the surface area of said catalyst composition is in the range of from about 20 $m^2/g$ to about 300 $m^2/g$, and said cobalt compound is selected from the group consisting of cobalt oxide and cobalt nitrate.

27. A process in accordance with claim 25, wherein the atomic ratio of Cu to Zn in said catalyst composition is in the range of from about 1:3 to about 3:1, the atomic ratio of Co to Cu is in the range of from about 1:1,000 to about 1:10, the surface area of said catalyst composition is in the range of from about 50 $m^2/g$ to about 200 $m^2/g$, and said cobalt compound is selected from the group consisting of cobalt oxide and cobalt nitrate.

28. A process in accordance with claim 19, wherein catalyst component (c) is rhenium or a compound of rhenium.

29. A process in accordance with claim 28, wherein the atomic ratio of Cu to Zn in said catalyst composition is in the range of from about 1:20 to about 20:1, the atomic ratio of Re to Cu is in the range of from about 1:50,000 to about 10:1, the surface area of said catalyst composition is in the range of from about 20 $m^2/g$ to about 300 $m^2/g$, and said rhenium compound is selected from the group consisting of rhenium oxide and ammonium perrhenate.

30. A process in accordance with claim 28, wherein the atomic ratio of Cu to Zn in said catalyst composition is in the range of from about 1:3 to about 3:1, the atomic ratio of Re to Cu is in the range of from about 1:5,000 to about 1:20, the surface area of said catalyst composition is in the range of from about 50 $m^2/g$ to about 200 $m^2/g$, and said rhenium compound is selected from the group consisting of rhenium oxide and ammonium perrhenate.

31. A process in accordance with claim 19, wherein said catalyst composition has been pretreated by heating with a reducing gas under such conditions as to partially reduce copper oxide before said contacting.

32. A process in accordance with claim 31, wherein said reducing gas is a free hydrogen containing gas, and said heating conditions comprise a temperature of about 350°–450° F. and a heating time of about 1–6 hours.

33. A process in accordance with claim 19, wherein said reaction conditions comprise a reaction temperature in the range of from about 200° to about 400° C., a reaction pressure in the range of from about 1 to about 5,000 psig, and a contact time in the range of from about 0.01 to about 60 minutes.

34. A process in accordance with claim 33, wherein said reaction conditions further comprise a combined gas hourly space velocity of said mixture comprising at least one primary aliphatic alcohol and carbon monoxide in the range of from about 100 to about 10,000 cc mixture/cc catalyst/hour, measured at about 550° F. and 15 psia.

35. A process in accordance with claim 19 comprising the additional step of (C) recycling at least a portion of said reaction product, from which at least a portion of said at least one ester has been separated in step (B), to the reaction zone.

36. A process in accordance with claim 19 wherein the formed ester is at least one of methyl formate and ethyl acetate.

* * * * *